(12) United States Patent
Stoval

(10) Patent No.: US 7,667,624 B2
(45) Date of Patent: Feb. 23, 2010

(54) METHODS AND APPARATUS FOR CLINICAL DATA COMPRESSION

(75) Inventor: William Murray Stoval, Draper, UT (US)

(73) Assignee: General Electric Company, Schenectady, NY (US)

( * ) Notice: Subject to any disclaimer, the term of this patent is extended or adjusted under 35 U.S.C. 154(b) by 45 days.

(21) Appl. No.: 11/625,568

(22) Filed: Jan. 22, 2007

(65) Prior Publication Data

US 2008/0177789 A1 Jul. 24, 2008

(51) Int. Cl.
*H03M 7/30* (2006.01)
*A61B 5/04* (2006.01)

(52) U.S. Cl. .......................... 341/50; 600/523; 707/101

(58) Field of Classification Search .................... 341/50, 341/51; 600/523; 707/101
See application file for complete search history.

(56) References Cited

U.S. PATENT DOCUMENTS

| | | | |
|---|---|---|---|
| 4,090,505 A * | 5/1978 | Mortara | ...................... 600/515 |
| 5,396,595 A | 3/1995 | Standley | |
| 6,161,043 A * | 12/2000 | McClure et al. | ................ 607/27 |
| 6,236,994 B1 | 5/2001 | Swartz et al. | |
| 6,839,003 B2 | 1/2005 | Soliman et al. | |
| 6,879,271 B2 | 4/2005 | Abdat | |
| 6,910,084 B2 | 6/2005 | Augustijn et al. | |
| 6,912,317 B1 | 6/2005 | Barnes et al. | |
| 7,180,943 B1 | 2/2007 | Arlid et al. | |
| 7,280,052 B2 | 10/2007 | Levy | |
| 7,310,648 B2 * | 12/2007 | Simske et al. | ................ 707/101 |
| 2006/0094968 A1 | 5/2006 | Drew | |
| 2007/0030177 A1 | 2/2007 | Monro | |

\* cited by examiner

*Primary Examiner*—Howard Williams
(74) *Attorney, Agent, or Firm*—Armstrong Teasdale LLP

(57) ABSTRACT

A method for compressing clinical data includes monitoring a clinical parameter of a patient using a digital electronic monitoring device, wherein the clinical parameter is a function of time. A processor is utilized to locate exceptional values of the clinical parameter in accordance with predetermined criteria. The method further includes electronically encoding and communicating diagnostically significant information concerning the exceptional values of the clinical parameters to a clinical database repository (CDR) and information concerning normal values of the clinical parameters to the CDR, wherein the communicated exceptional values of clinical parameters and the communicated normal values of clinical parameters are encoded using different methods.

20 Claims, 5 Drawing Sheets

METHODS AND APPARATUS FOR CLINICAL DATA COMPRESSION

BACKGROUND OF THE INVENTION

This invention relates generally to clinical databases and more particularly to methods and apparatus for collecting and storing large amounts of clinical data.

Clinical database repositories (CDRs) are databases that are usually used by a plurality of different hospitals or organizations to store and analyze patient data. These repositories can be used to store a great deal of data concerning patients. For example, a patient may be on an electrocardiograph machine for six hours to discover one or more heart palpitations. At least one known method for storing such information on a CDR involves storing the entire electrocardiogram, in full form, in the CDR. Such an electrocardiogram requires a considerable amount of storage space in the CDR, yet this volume of data from individual patients is not unusual. Even though there is an ever-increasing amount of data that needs to be stored, and the amount of information that is purged is typically very small. As a result, CDRs are rapidly becoming unmanageably large. Many CDR databases already measure in the Terabytes, and continue to grow by the day.

BRIEF DESCRIPTION OF THE INVENTION

In one aspect, some configurations of the present invention provide a method for compressing clinical data. The method includes monitoring a clinical parameter of a patient using a digital electronic monitoring device, wherein the clinical parameter is a function of time. A processor is utilized to locate exceptional values of the clinical parameter in accordance with predetermined criteria. The method further includes electronically encoding and communicating diagnostically significant information concerning the exceptional values of the clinical parameters to a clinical database repository (CDR) and information concerning normal values of the clinical parameters to the CDR, wherein the communicated exceptional values of clinical parameters and the communicated normal values of clinical parameters are encoded using different methods.

In another aspect, some configurations of the present invention provide a digital electronic monitoring device suitable for generating compressed clinical data and sending the compressed data to a clinical database repository (CDR). The device includes a sensor configured to monitor a clinical parameter of a patient, wherein the monitored clinical parameter is a function of time, and a locator module configured to locate exceptional values of the clinical parameter in accordance with predetermined criteria. The device also includes an electronic encoder and communicator module configured to communicate diagnostically significant information concerning the exceptional values of the clinical parameters to the CDR and information concerning normal values of the clinical parameters to the CDR, wherein the communicated exceptional values of clinical parameters and the communicated normal values of clinical parameters are encoded by the electronic encoder and communicator module using different encoding methods.

In yet another aspect, some configurations of the present invention provide a method for compressing clinical data. The method includes monitoring a clinical parameter of a patient using a digital electronic monitoring device, wherein the clinical parameter is a function of time. Clinical values are transmitted to a clinical database repository (CDR) and retained for a period of time. Then later, the method includes locating exceptional values of the clinical parameter in the CDR in accordance with predetermined criteria, electronically encoding diagnostically significant information concerning the exceptional values of the clinical parameters and information concerning normal values of the clinical parameters, wherein the exceptional values of clinical parameters and the normal values of clinical parameters are encoded using different methods, and replacing the retained clinical values in the CDR with the differently encoded exceptional values of the clinical parameters and the encoded normal values of the clinical parameters to thereby save storage space in the CDR.

It will be appreciated that some configurations of the present invention provide an effective, efficient, and economical way for storing data, as compared to other methods and apparatus that merely do transforms on stored data to find different ways of extracting interesting information.

Figure 1:
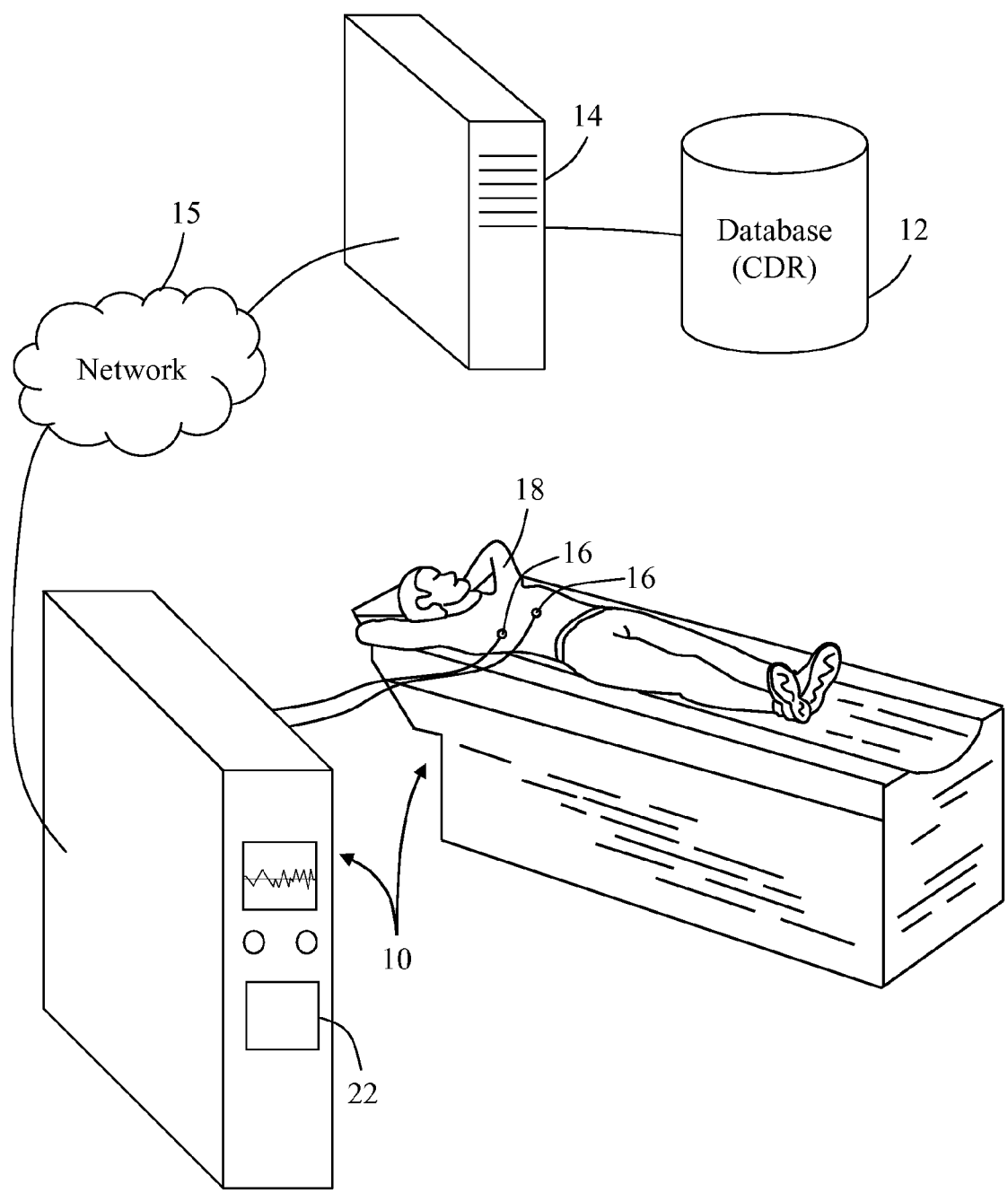
FIG. 1 is a pictorial block diagram of a configuration of a digital electronic monitoring device communicating with a clinical database repository.

It will be appreciated that configurations of the present invention provide an efficient, economical, and effective way to store data, as compared to other methods and apparatus that merely do transforms on large amounts of stored data to find different ways of extracting interesting information.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry or software/firmware modules. Thus, for example, one or more of the functional blocks (e.g., processors or memories) may be implemented in a single piece of hardware (e.g., a general purpose signal processor or a block or random access memory, hard disk, or the like). Similarly, programs may be stand alone programs, subroutines, or packages, and the like. The various embodiments are not limited to the arrangements and instrumentality shown in the drawings.

As used herein, an element or step recited in the singular and proceeded with the word "a" or "an" should be understood as also including within its scope plural said elements or steps, unless explicitly excluded. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 2:
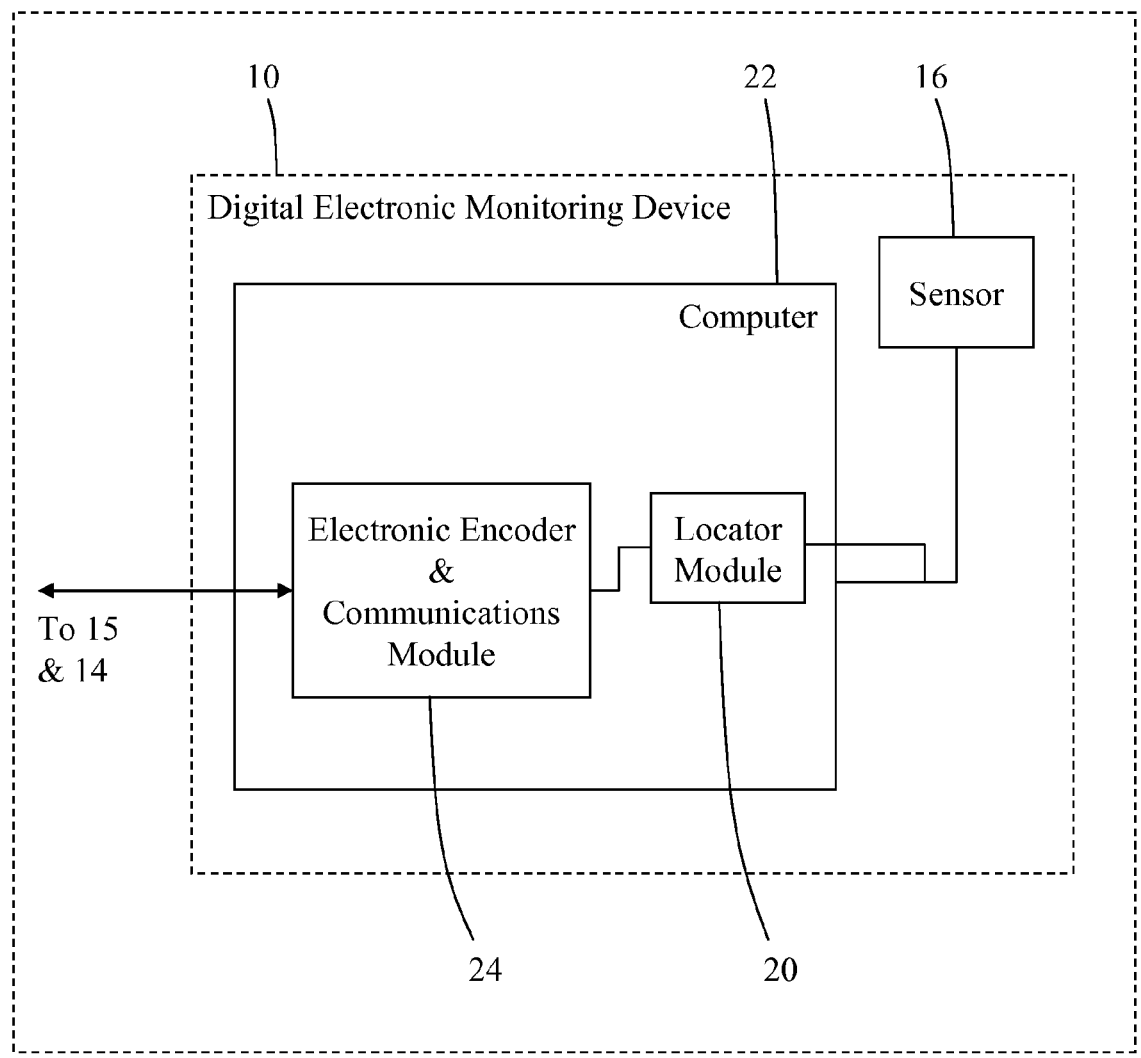
FIG. 2 is a block diagram of a configuration of a digital electronic monitoring device.

In some configurations of the present invention and referring to FIGS. 1 and 2, a digital electronic monitoring device 10 is provided. Digital electronic monitoring device 10 is suitable for generating compressed clinical data and sending the compressed data via any known means to a clinical database repository (CDR) 12. For example, in at least one configuration, clinical database repository resides on a remote server 14 communicating with devices over a network 15 such as the Internet and/or an intranet. In at least one other configuration not shown in the Figures, CDR 12 resides in a stand-alone dedicated computer or workstation which may, but need not reside in digital electronic monitoring device 10 and which may, but need not, also control digital electronic monitoring device 10. Device 10 includes a sensor 16 configured to monitor a clinical parameter of a patient 18, wherein the monitored clinical parameter is a function of time. (For purposes of the present invention, the term "function of time" also includes within its scope parameters gathered a plurality of times over a period of time.) For example, in some configurations and with an appropriate sensor 16, the clinical parameter may be an electrocardiogram signal, the patient's heart rate, or the patient's breath rate or breath volume (i.e., the amount of air being taken in per breath), however, this list of clinical parameters is not exhaustive. Furthermore, the invention does not exclude configurations in which more than one clinical parameter is monitored.

Device 10 also includes a locator module 20 that is configured to locate exceptional values of the clinical parameter in accordance with predetermined criteria. Locator module 20 locates the exceptional values of the clinical parameter prior to these values being stored in CDR 12. (A "module" is defined herein as a software or firmware subroutine, program or other set of instructions, or hardware that performs a particular function, or some combination of software, firmware, and/or hardware.) Locator module 20 can run on a processor or computer 22 that can be, but need not be the same as the stand-alone computer described above. Also, processor or computer 22 can be, but need not be, internal to device 10. For purposes of the present invention, the term "processor" shall be used in the broad sense to include within its scope not only particular components of a computer, but also processors and other ancillary components, such as memory, I/O ports, displays, etc. Thus, the term "processor," as used herein, can also include within its scope a computer or workstation.

Device 10 further includes an electronic encoder and communicator module 24 configured to communicate diagnostically significant information concerning the exceptional values of the clinical parameter to CDR 12 and information concerning normal values of the clinical parameter to CDR 12, wherein the communicated exceptional values of clinical parameters and the communicated normal values of clinical parameters are encoded by electronic encoder and communicator module 24 using different encoding methods. In many configurations of the present invention, electronic encoder and communicator module 24 encodes normal values of the clinical parameter so that storage of the normal values (which are diagnostically uninteresting) requires less storage space in CDR 12 than an equivalent length of time or quantity of diagnostically significant information about exceptional values of the clinical parameter. In other words, in many configurations of the present invention, there is less information communicated to and stored in CDR 12 about normal values than about exceptional values.

Figure 3:
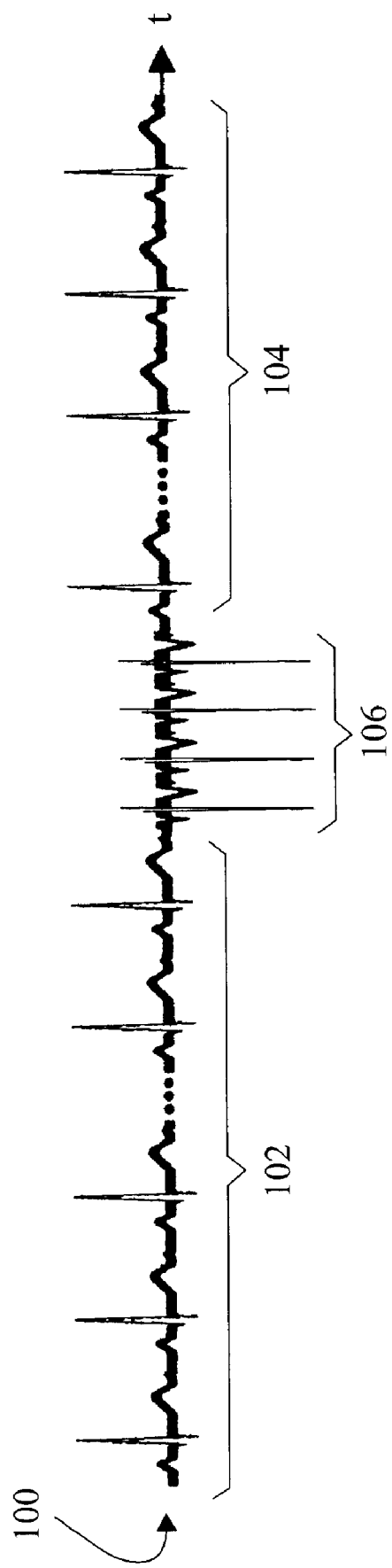
FIG. 3 is a drawing of an electrocardiogram of a patient, showing long sequences of normal data and a short sequence of diagnostically significant data. Ellipses are used in FIG. 3 as placeholders to indicate omitted portions of the electrocardiogram

In some configurations, device 10 is configured to "run length" encode the information concerning the normal values of clinical parameters. Run length encoding is a method of encoding wherein, for example, a long sequence of function values or events (e.g., three hours of normal heartbeats) is compressed by replacing the long sequence with a much shorter sequence comprising an indication of, for example, the length of time or number of events in the long sequence and an indication of the function value, range of function values, or type of event occurring in that length of time or number of events. Also, there may be other information associated with the run length encoded information, such as a start time and/or stop time. For example, and referring to FIG. 3, an electrocardiogram parameter 100 is shown. During the first three hours of data collection 102, electrocardiogram parameter 100 is within a set of predetermined criteria (which, in some configurations, can be entered by an attendant, nurse, or physician). For example, the predetermined criteria may include limits defining a normal heart rate. The heart rate represented with the first three hours of data collection 102 is 1.05 averages beats per second, or 63 beats per minute, with no two consecutive heartbeats outside of a 50 to 80 beat per second range. Thus, the first three hours of data collection 102 of electrocardiogram parameter 100 are encoded, in at least one configuration, as 90909090134515020406030000635080091919191, wherein "90909090" is a marker indicating that the following data sequence is run length encoded, "134515020406" represents the start time of the sequence (fifteen seconds after 1:45 p.m. on the second day of April, 2006), "030000" represents a run time of 3 hours, 0 minutes, and 0 second, "635080" represents an average heart rate of 65, with a minimum of 50 and a maximum of 80 within the run time, and 91919191 represents the end of run length encoded data. A similar encoding is given to the last three hours of data collection 104. It will be understood that the coding method described above is given only as an example. Other encoding methods can be used, including other than run length encoding. For example, a coarser amplitude encoding and/or a longer time interval can be used for normal values of clinical parameters than for exceptional values of clinical parameters. In some configurations, data is stored in relational database fields, with exceptional values of the clinical parameters stored in a "findings" table with greater detail than the encoded data, and "normal" data stored in a table having columns for start time, start date, and either run-time or end date. Also, in some configurations, minimum and maximum bounds that define "normality" can be stored as columns in the table.

The different coding methods used by electronic encoder and communicator module 24 to encode the communicated exceptional values of clinical parameters and the communicated normal values of clinical parameters can be run length encoding, described above, for normal values of clinical parameters, and a time series of values for the communicated diagnostically significant information. For example, diagnostically significant information can comprise heart palpitations 106 recorded in electrocardiogram signal 100. Heart palpitations 106 may occur rarely and infrequently within electrocardiogram signal 100, but their diagnostic significance may require that as much information as possible about the heart palpitations be preserved. Thus, a time series of amplitude values of electrocardiogram signal 100 is communicated to CDR 12 for heart palpitations 106. The time series of amplitude values can be, for example, eight bit signed amplitude values at intervals of 0.01 or 0.001 sec., or any other predetermined number of bits at any other predetermined interval. Thus, not only is the coding for communicated exceptional values of clinical parameters and the communicated normal values of clinical parameters, but the "compression" achieved by the encoding of communicated normal values significantly reduces the size and space of CDR 12, as well as the time to search for diagnostically significant values. Furthermore, by identifying diagnostically significant exceptional values prior to entering them in CDR 12, additional data mining operations for finding interesting patient abnormalities is made easier or even, in some cases, unnecessary.

In the above examples, sensor 16 of device 10 is an electrocardiograph sensor configured to monitor an electrocardiogram signal 100 as the clinical parameter of a patient 18. However, device 10 can be configured to accept a different sensor or sensors 16 either instead of an electrocardiograph sensor or in addition to an electrocardiograph sensor, or it may be configured with a fixed electrocardiograph sensor and/or one or more other types of sensors 16. For example, in some configurations of the present invention, sensor 16 is a heart rate monitor sensor and the clinical parameter is the patient's heart rate. In yet another configuration of the present invention, sensor 16 is a sleep apnea sensor and the clinical parameter is at least one of the patient's breath rate and the patient's breath volume. These different types of sensors are given only by way of example, and not by limitation.

Figure 4:
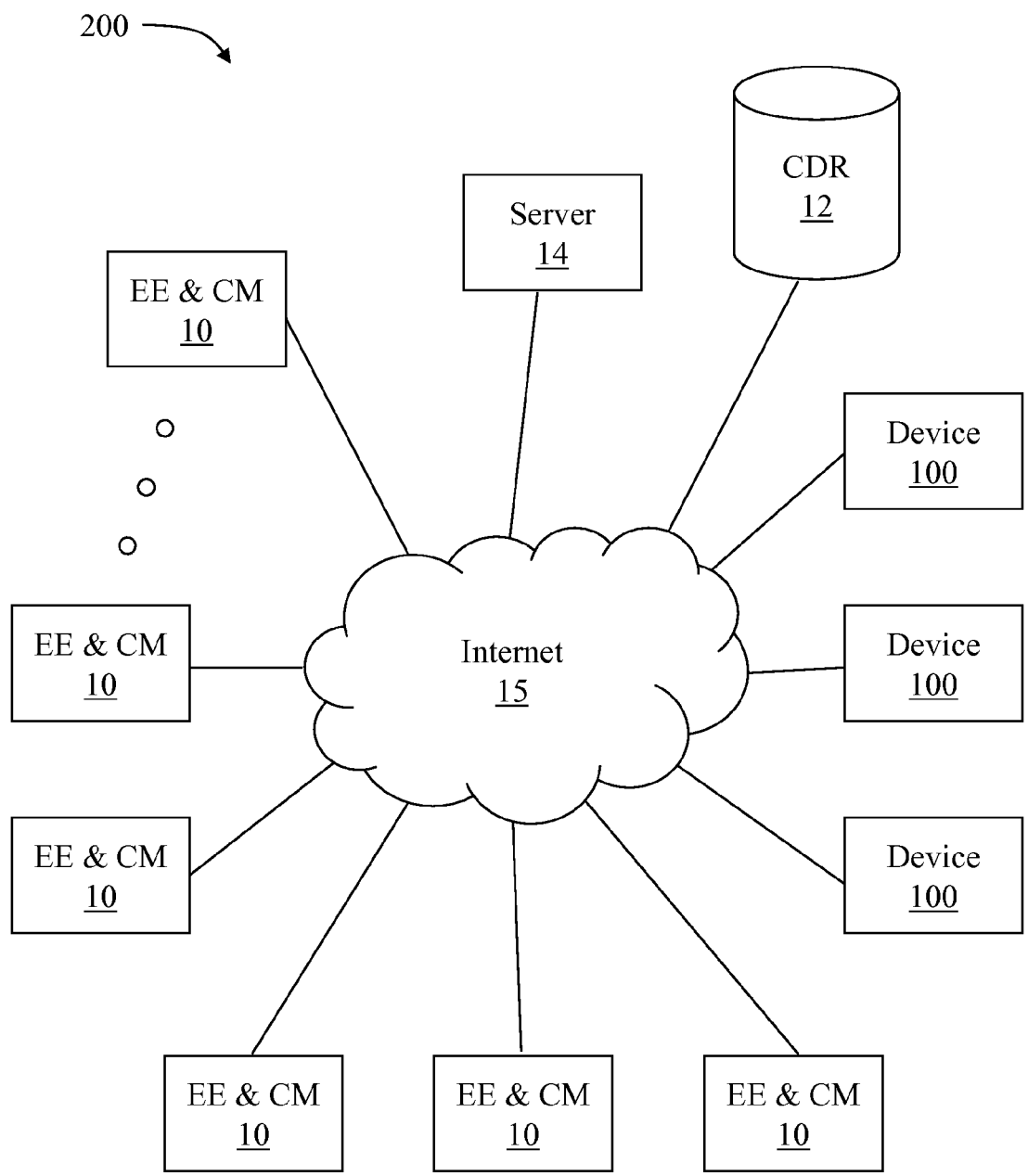
FIG. 4 is a block diagram of a network configuration suitable for use in an environment including a plurality of hospitals.

In some configurations of the present invention and referring to FIG. 4, a network 200 (public, private, and/or virtual) is provided having at least one digital electronic monitoring device 10. (For purposes of the present invention, an analog device with a digital converter between it and the CDR system is considered within the scope of the term "digital electronic monitoring device.") Many more such devices 10 may also be part of network 200, as would be expected in a large hospital network or in a network aggregating data from a plurality of hospitals. A database server 202 is provided that is configured to store the differently encoded communicated exceptional values of clinical parameters and the communicated normal values of clinical parameters in CDR 12, which may reside in database server 14. Also, in some configurations, database server 14 and CDR 12 are further configured to store records wherein exceptional values of clinical parameters and communicated normal values of clinical parameters are encoded by an identical method. Thus, some hospitals, for example, could use devices 100 that have not been converted and/or do not provide different encodings for normal and for exceptional data, and over time, these hospitals can convert to the preferred different encoding methods.

Figure 5:
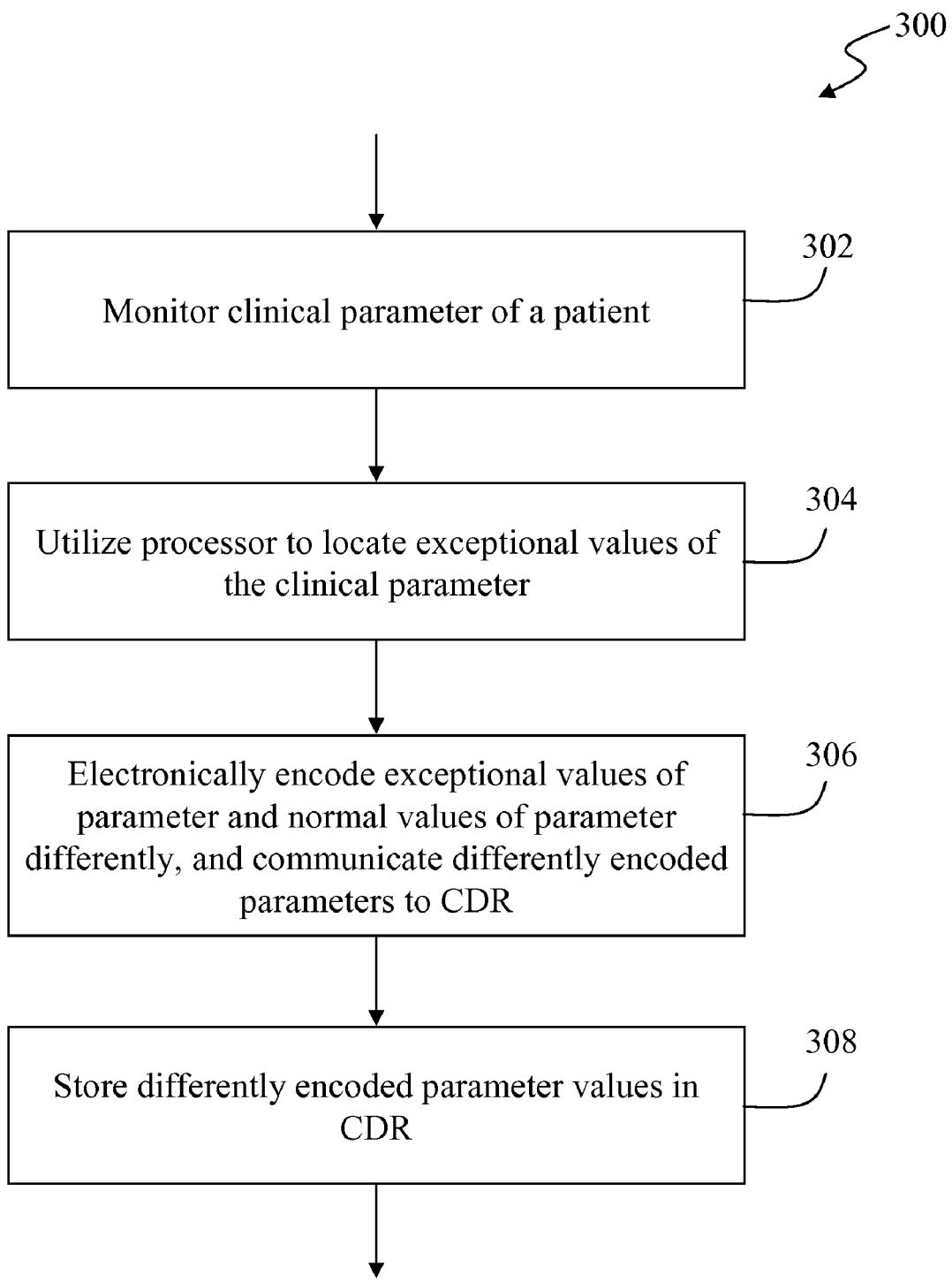
FIG. 5 is a block diagram of a method configuration of the present invention.

In some configurations of the present invention and referring to flow chart 300 of FIG. 5, a method for compressing clinical data is provided. The method includes, at 302, monitoring a clinical parameter of a patient using a digital electronic monitoring device, wherein the clinical parameter is a function of time. As a subsequent operation, at 304, the method further includes utilizing a processor to locate exceptional values of the clinical parameter in accordance with predetermined criteria. As a still further subsequent operation, at 306, the method further includes electronically encoding and communicating diagnostically significant information concerning the exceptional values of the clinical parameters to a clinical database repository (CDR) and information concerning normal values of the clinical parameters to the CDR, wherein the communicated exceptional values of clinical parameters and the communicated normal values of clinical parameters are encoded using different methods. The encoding at 306 may comprise run length encoding of the normal values of the clinical parameter. The encoding at 306 may further comprise encoding a time series of values of the monitored clinical value for the communicated diagnostically significant information.

In the above-described method, the digital electronic monitoring device can be an electrocardiograph machine, and the clinical parameter can be an electrocardiogram signal. At 306, the encoding of the communicated normal values of the clinical parameter can comprise encoding a length of time during which the electrocardiogram signal is within normal values according to the predetermined criteria and the encoding of the communicated diagnostically significant information can comprise encoding the time varying electrocardiogram signal during a period within a length of time during which the electrocardiogram signal is outside of the normal values.

In some configurations of the above-described method, the digital electronic monitoring device can be a heart rate monitor, a sleep apnea monitor, or a vital sign monitor, and the clinical parameter is a corresponding member of the group consisting of the patient's heart rate, the patient's breathing rate or volume, and a vital sign of the patient. The digital electronic monitoring device may, in some configurations, be a device that receives laboratory data or general clinical observations.

Also, some configurations of the present invention further include, at 308, storing the differently encoded communicated exceptional values of clinical parameters and the communicated normal values of clinical parameters in CDR 12. In some configurations of the present invention, some patients' exceptional values of clinical parameters and normal values of clinical parameters may be encoded by an identical method, while other patents' exceptional values of clinical parameters and normal values of clinical parameters may be encoded separately by different methods, as it is not necessary that the encoding by different methods be adopted by an entire organization or group of hospitals sharing a CDR at the same time.

In some configurations of the present invention, instead of communicating encoded data to the CDR, all of the data is sent encoded in the same manner, without loss of information (i.e., in a form in which all of the original measurements can be recovered), while the patient encounter is active (and possibly for some specified period of time after the encounter). Once the patient is no longer being cared for, the system then encodes the data using methods described herein to save space, because the data may never be looked at again. In this manner, the same performance as currently known systems is achieved while the patient is being cared for, and the only sacrifice is possibly longer retrieval and display times after the patient is no longer being actively cared for. Such configurations may represent a desirable trade-off because, except in relatively rare cases such as those involving research studies, it is doubtful that anyone would want to look at the full level of level of detail after the patient is no longer being cared for.

Thus, it will be appreciated that configurations of the present invention provide an efficient, economical, and effective way to store data, as compared to other methods and apparatus that merely do transforms on large amounts of stored data to find different ways of extracting interesting information.

While the invention has been described in terms of various specific embodiments, those skilled in the art will recognize that the invention can be practiced with modification within the spirit and scope of the claims.

What is claimed is:

1. A method for compressing clinical data, said method comprising:

selecting a first encoding method and a second encoding method, the first encoding method and the second encoding method being fixed during a monitoring session of a first patient, the second encoding method providing a compression ratio that is higher than a compression ratio provided by the first encoding method;

monitoring a clinical parameter of the first patient during the monitoring session using a digital electronic monitoring device, wherein the clinical parameter is a function of time;

locating exceptional values of the clinical parameter in accordance with predetermined criteria using a processor;

electronically encoding diagnostically significant information concerning the exceptional values of the clinical parameters using the first encoding method;

electronically encoding information concerning normal values of the clinical parameters, wherein the normal values of clinical parameters and the predetermined criteria are encoded using the second encoding method; and communicating the differently encoded exceptional values of clinical parameters, the normal values of clinical parameters, and the predetermined criteria to a clinical database repository (CDR).

2. A method in accordance with claim 1 wherein electronically encoding information concerning normal values of the clinical parameter comprises run length encoding the information concerning the normal values of clinical parameters.

3. A method in accordance with claim 1 wherein electronically encoding diagnostically significant information comprises encoding a time series of values of the monitored clinical parameter.

4. A method in accordance with claim 1 wherein the digital electronic monitoring device is an electrocardiograph machine.

5. A method in accordance with claim 4 wherein the clinical parameter is the electrocardiogram signal.

6. A method in accordance with claim 5 wherein electronically encoding information concerning normal values of the clinical parameter comprises encoding a length of time during which the electrocardiogram signal is within normal values according to the predetermined criteria and electronically encoding diagnostically significant information comprises encoding the time varying electrocardiogram signal during a period within a length of time during which the electrocardiogram signal is outside of the normal values.

7. A method in accordance with claim 1 wherein the digital electronic monitoring device is one of a heart rate monitor, a sleep apnea monitor, and a vital sign monitor.

8. A method in accordance with claim 1 further comprising storing the differently encoded communicated exceptional values of clinical parameters, the communicated normal values of clinical parameters, and the predetermined criteria in the CDR.

9. A method in accordance with claim 8, further comprising, for at least a second patient:
monitoring said clinical parameter of the second patient;
electronically encoding exceptional values of the second patient's clinical parameters and normal values of the second patient's clinical parameters using identical encoding methods; and
communicating the encoded clinical parameters of the second patient to the CDR.

10. A digital electronic monitoring device suitable for generating compressed clinical data and sending the compressed data to a clinical database repository (CDR), said device comprising:

a sensor configured to monitor a clinical parameter of a patient during a monitoring session, wherein the monitored clinical parameter is a function of time;

a locator module configured to locate exceptional values of the clinical parameter in accordance with predetermined criteria; and an electronic encoder and communicator module configured to:
set a first encoding method and a second encoding method, the first encoding method and the second encoding method being fixed during the monitoring session, the second encoding method providing a compression ratio that is higher than a compression ratio provided by the first encoding method;
encode diagnostically significant information concerning exceptional values of the clinical parameters using the first encoding method;
encode the predetermined criteria and information concerning normal values of the clinical parameters using the second encoding method; and
communicate the diagnostically significant information concerning the exceptional values of the clinical parameters, the predetermined criteria, and the information concerning the normal values of the clinical parameters to the CDR.

11. A device in accordance with claim 10, wherein said electronic encoder and communicator module is configured to run length encode the information concerning the normal values of the clinical parameters.

12. A device in accordance with claim 10, wherein said electronic encoder and communicator module is configured to encode the diagnostically significant information as a time series of values.

13. A device in accordance with claim 10 wherein the sensor is an electrocardiograph sensor configured to generate an electrocardiogram signal.

14. A device in accordance with claim 13 wherein the clinical parameter is the electrocardiogram signal.

15. A device in accordance with claim 14, wherein said electronic encoder and communicator module is configured to:
encode a length of time during which the electrocardiogram signal is within normal values according to the predetermined criteria using the second encoding method; and
encode the time varying electrocardiogram signal during a period within a length of time during which the electrocardiogram signal is outside of the normal values using the first encoding method.

16. A device in accordance with claim 10 wherein said sensor comprises one of a heart rate monitor sensor, a sleep apnea monitor, and a vital sign monitor, and the clinical parameter is a corresponding one of the patient's heart rate, the patient's breathing rate or volume, and a vital sign of the patient.

17. A network having at least one device in accordance with claim 10 and a database server configured to store the differently encoded communicated exceptional values of clinical parameters and the communicated normal values of clinical parameters in the CDR.

18. A network in accordance with claim 17 wherein the database server and CDR are configured to store records of the exceptional values of the clinical parameters and the normal values of the clinical parameters that are encoded by an identical encoding method.

19. A method for compressing clinical data, said method comprising:

selecting a first encoding method and a second encoding method, the first encoding method and the second encoding method being fixed during a monitoring session of a patient, the second encoding method providing a compression ratio that is higher than a compression ratio provided by the first encoding method;

monitoring a clinical parameter of the patient using a digital electronic monitoring device during the monitoring session, wherein the clinical parameter is a function of time;

electronically encoding the clinical parameter of the patient and predetermined criteria;

transmitting the encoded clinical parameter and the encoded predetermined criteria to a clinical database repository (CDR);

retaining the clinical parameter and the predetermined criteria in the CDR for a predetermined period of time;

then later, locating exceptional values of the clinical parameter in the CDR in accordance with the predetermined criteria;

electronically encoding diagnostically significant information concerning the exceptional values of the clinical parameter using the first encoding method;

electronically encoding information concerning normal values of the clinical parameter using the second encoding method; and replacing the retained clinical values in the CDR with the encoded exceptional values of the clinical parameter and the encoded normal values of the clinical parameter.

20. A method in accordance with claim 19 wherein said locating, said electronically encoding, and said replacing is performed after the patient is no longer being cared for.

* * * * *